(12) United States Patent
Reddick

(10) Patent No.: US 11,457,953 B2
(45) Date of Patent: Oct. 4, 2022

(54) EXTERNAL FIXATION ALIGNMENT GAUGE

(71) Applicant: J & A Medical LLC, Norman, OK (US)

(72) Inventor: Joseph D. Reddick, Norman, OK (US)

(73) Assignee: J & A Medical LLC, Norman, OK (US)

( * ) Notice: Subject to any disclaimer, the term of this patent is extended or adjusted under 35 U.S.C. 154(b) by 396 days.

(21) Appl. No.: 16/761,182

(22) PCT Filed: Aug. 29, 2018

(86) PCT No.: PCT/US2018/048557
§ 371 (c)(1),
(2) Date: May 1, 2020

(87) PCT Pub. No.: WO2019/046435
PCT Pub. Date: Mar. 7, 2019

(65) Prior Publication Data
US 2020/0352604 A1    Nov. 12, 2020

Related U.S. Application Data

(60) Provisional application No. 62/554,173, filed on Sep. 5, 2017, provisional application No. 62/553,000, filed on Aug. 31, 2017.

(51) Int. Cl.
*A61B 17/66* (2006.01)
*G01B 3/00* (2006.01)
(Continued)

(52) U.S. Cl.
CPC .............. *A61B 17/66* (2013.01); *G01B 3/004* (2013.01); *G01B 3/04* (2013.01); *A61B 2090/376* (2016.02); *A61B 2090/3966* (2016.02)

(58) Field of Classification Search
USPC ....................................... 606/54, 56; 33/512
See application file for complete search history.

(56) References Cited

U.S. PATENT DOCUMENTS 941,687 A    11/1909  Page
D282,277 S    1/1986  Kenna
(Continued)

FOREIGN PATENT DOCUMENTS

| CN | 109069187 B | * | 1/2022 | ............. A61B 17/62 |
| GB | 2138300 A | * | 10/1984 | ............. A61B 17/62 |

(Continued)

OTHER PUBLICATIONS

International Search Report dated Dec. 31, 2018, in PCT/US2018/048557, filed Aug. 29, 2018.
(Continued)

*Primary Examiner* — Christopher W Fulton
(74) *Attorney, Agent, or Firm* — Dunlap Codding, P.C.

(57) ABSTRACT

A device for use with orthopedic surgical fixation devices, and more particularly, to an alignment gauge for use with an external fixation system comprising one or more support members (rings, plates, etc.) connected to one or more bone members wherein a plurality of struts of adjustable length support and/or connect the one or more support members. The alignment gauge indicating to a user, such as a surgeon, the degree of translational offset between one bone member and a center point of at least one of the support members in at least one of an anterior-posterior or medial-lateral plane.

16 Claims, 8 Drawing Sheets

(51) Int. Cl.
*G01B 3/04* (2006.01)
*A61B 90/00* (2016.01)

(56) References Cited

U.S. PATENT DOCUMENTS

| | | | |
|---|---|---|---|
| 4,768,524 A * | 9/1988 | Hardy | A61B 17/62 606/54 |
| 5,049,150 A | 9/1991 | Cozad | |
| D322,851 S | 12/1991 | Pilling | |
| D364,542 S | 11/1995 | Pollard | |
| 5,702,389 A * | 12/1997 | Taylor | A61B 17/62 606/56 |
| 5,885,282 A * | 3/1999 | Szabo | A61B 17/62 606/56 |
| 6,030,386 A * | 2/2000 | Taylor | A61B 17/62 606/56 |
| 6,129,727 A * | 10/2000 | Austin | A61B 17/62 606/56 |
| D579,562 S | 10/2008 | Anderson et al. | |
| D598,096 S | 8/2009 | Petersen | |
| D600,346 S | 9/2009 | Petersen | |
| D643,921 S | 8/2011 | Davilla et al. | |
| D646,386 S | 10/2011 | Miller et al. | |
| D667,952 S | 9/2012 | Zona et al. | |
| 8,377,060 B2 * | 2/2013 | Vasta | A61B 17/60 606/56 |
| 9,017,339 B2 * | 4/2015 | Edelhauser | A61B 90/06 33/512 |
| D745,169 S | 12/2015 | Sztuk | |
| D750,776 S | 3/2016 | Lytle et al. | |
| 9,717,528 B2 * | 8/2017 | Singh | A61B 17/62 |
| D799,696 S | 10/2017 | Sahhar | |
| D888,947 S | 6/2020 | Reddick | |
| D900,586 S | 11/2020 | Pille | |
| 2003/0191466 A1 * | 10/2003 | Austin | A61B 17/62 606/54 |
| 2004/0249375 A1 | 12/2004 | Agee et al. | |
| 2007/0055234 A1 * | 3/2007 | McGrath | A61B 17/62 606/56 |
| 2007/0084071 A1 | 4/2007 | Charpentier | |
| 2009/0177198 A1 * | 7/2009 | Theodoros | A61B 17/62 606/56 |
| 2010/0268228 A1 | 10/2010 | Petersen | |
| 2011/0208187 A1 | 8/2011 | Wong | |
| 2014/0031822 A1 | 1/2014 | Venturini et al. | |
| 2014/0288486 A1 | 9/2014 | Hart et al. | |
| 2016/0000465 A1 * | 1/2016 | Ross | A61B 90/39 606/56 |
| 2016/0042571 A1 | 2/2016 | Mikheev et al. | |
| 2016/0066956 A1 * | 3/2016 | Siemer | A61B 17/6416 606/56 |
| 2020/0352604 A1 | 11/2020 | Reddick | |
| 2021/0219993 A1 | 7/2021 | Matusaitis et al. | |

FOREIGN PATENT DOCUMENTS

| | | | | |
|---|---|---|---|---|
| WO | WO-2012102685 A1 * | 8/2012 | | A61B 17/62 |
| WO | WO-2019046435 A1 * | 3/2019 | | A61B 17/62 |

OTHER PUBLICATIONS

Written Opinion of the international Searching Authority dated Dec. 31, 2018, in PCT/US2018/048557, filed Aug. 29, 2018.
U.S. Appl. No. 29/739,778; Joseph D. Reddick, filed May 1, 2020; Office Action dated Oct. 27, 2021.

* cited by examiner

EXTERNAL FIXATION ALIGNMENT GAUGE

CROSS REFERENCE TO RELATED APPLICATIONS/INCORPORATION BY REFERENCE STATEMENT

The present application claims the benefit under 35 U.S.C 119(e) of U.S. Provisional Application No. 62/553,000, filed Aug. 31, 2018, and Provisional Application No. 62/554,173 filed Sep. 5, 2017. The entirety of which are hereby expressly incorporated herein by reference.

TECHNICAL FIELD

The present disclosure relates generally to a device for use with orthopedic surgical fixation device. The present disclosure also relates to a method of measuring a translation distance between a first bone member and a center point of a first support member.

BACKGROUND

Field of the Invention

The inventive concepts disclosed and claimed herein relate generally to a device for use with orthopedic surgical fixation devices, and more particularly, to an alignment gauge for use with an external fixation system comprising one or more support members (rings, plates, etc.) connected to one or more bone members wherein a plurality of struts of adjustable length support and/or connect the one or more support members. The alignment gauge indicating to a user, such as a surgeon, the degree of translational offset between one bone member and a center point of at least one of the support members in at least one of an anterior-posterior or medial-lateral plane.

General Background of the Invention

It is often necessary to realign, reposition and/or securely hold two elements relative to one another. For example, in the practice of medicine, bone members (e.g., bone fragments or segments of a broken bone) and the like must sometimes be aligned or realigned and repositioned to restore boney continuity and skeletal function. After realignment and repositioning, skeletal stabilization with a cast, plate and screws, intramedullary devices, or external skeletal fixators can occur.

Certain boney skeletal injuries or conditions are sometimes treated with an external frame that is attached to the boney skeleton with threaded and/or smooth pins and/or threaded and/or smooth and/or beaded wires. Such constructs are commonly referred to as orthopedic external fixators or external skeletal fixators. External fixators may be utilized to treat acute fractures of the skeleton, soft tissue injuries, delayed union of the skeleton when bones are slow to heal, nonunion of the skeleton when bones have not healed, malunion whereby broken or fractured bones have healed in a malposition, congenital deformities whereby bones develop a malposition, and bone lengthening, widening, or twisting.

External fixator frames vary considerably in design and capabilities, and may include multiple or single bars or rods, and a plurality of clamps for adjustably securing the bars to pins or wires which are, in turn, joined to the boney skeleton. The pins or wires may extend completely through the boney skeleton extending out each side of the limb or may extend through the boney skeleton and out one side of the limb. Pins that extend completely through the boney skeleton and out both sides of the limb are commonly referred to as "transfixation pins." Pins that extend through the boney skeleton and out only one side of the limb are commonly referred to as "half pins." Such external fixator frames may be circumferential for encircling a patient's body member (e.g., a patient's tibia), or may be semi-circumferential or even unilateral and thereby extending solely along one side of a patient's body member. Materials for the components comprising the frames also vary, including metals, alloys, plastics, composites, and ceramics.

A circumferential external fixator system, for example, but not by way of limitation, was disclosed by G. A. Ilizarov during the early 1950s. The Ilizarov system included at least two rings or "halos" that encircle a patient's body member (e.g., a patient's leg), connecting rods extending between the two rings, transfixion pins that extend through the patient's bone structure, and connectors for connecting the transfixion pins to the rings. Use of the Ilizarov system to deal with angulation, translation, and rotation is disclosed in "Basic Ilizarov Techniques," Techniques in Orthopaedics®, Vol. 5, No. 4, December 1990, pages 55-59, for example, the entire contents of which are hereby incorporated by reference in their entirety.

A circumferential external fixator system was disclosed by Austin et al. in U.S. Pat. No. 6,129,727 (the entire contents of which are hereby incorporated by reference in their entirety) as providing an update to the Ilizarov system. In particular, Austin et al. disclosed a spatial frame fixation apparatus that utilized a plurality of support struts of equal length to support a pair of frame members such as circular rings affixed to respective bone parts with pins. More particularly, Austin et al. disclosed a dynamic external fixation system whereby the elongated support struts had a position adjusting member that changed the distance between an end of a strut and the adjacent ring or like support member. Through such adjustment, the bone parts were incrementally moved into proper alignment according to a "prescription" or set of instructions that could be implemented by a medical technician and/or the patient.

International Publication Number WO 03/086212 (the entire contents of which are hereby incorporated by reference in their entirety) disclosed another external fixator system and methods of using same for aligning fragments of a fractured bone or, alternatively, for positioning bones. The system disclosed in the '212 publication includes the use of a computer in aiding the positioning of the external fixator system with respect to the bones as well as for calculating the "prescription" for incrementally aligning the bones. Through operations on a computer model, desired placement, movement, and final alignment of the bones is determined. The computer model requires certain inputs relating to the placement and orientation of the bones to one another, placement of the rings of the external fixation device, the lengths of the struts extending between these rings, and the position of at least one of the bones with respect to at least one of the circular rings. The computer model takes these inputs and, by using certain mathematical algorithms, provides the "prescription" for adjusting the length of each individual strut over time to thereby incrementally move the bone fragments into a desired alignment with respect to one another.

Despite the algorithmic precision claimed in the '212 publication, it is well known drawback of the current external fixation systems utilizing adjustable struts and computer alignment that the surgeon is required to approximate some of the numerical inputs required to complete the computer aided alignment. For example, but not by way of limitation, the surgeon is required to approximate the amount of translation between the center point of at least one of a proximal or distal circular fixation ring and its corresponding bone member. The amount of translation is determined in an anterior-posterior plane as well as in a medial-lateral plane. To date, surgeons have approximated these values by laying measuring tools on radiographs and/or drawing intersecting rays on the radiograph and thereafter calculating the degree of translation between the bone members. Such inexact estimates as to the degree of translation oftentimes lead to inaccurate computer aided alignment "prescriptions" Thereby extending the time period in which the external fixation system is attached to the patient.

SUMMARY

The presently claimed and disclosed inventive concept(s) provides an external fixation alignment gauge that is used with support members (e.g., rings or plates) that are held in spaced apart relationship with a plurality of adjustable length struts. Support members of this type are used, for example, in Ilizarov procedures wherein bone pins supported by the support members extend to the bone tissue. The alignment gauge has a body member having a first end, a second end, a front face, a back face, a top face, and a bottom face. At least the front face has a plurality of markings serving as indicia of distance.

In one embodiment, the alignment gauge is used with an external fixator system having at least a first and second support member each connected to a first and second bone member, respectively. This external fixator system also includes a plurality of struts with each strut having one end pivotally connected to the first support member, another end pivotally connected to the second support member, and each strut having an adjustable length. This external fixator system may, in some embodiments, further include an elongate member having a first portion that is alignable with the first bone member (for example, but by way of limitation, a longitudinal axis extending through the center of the first bone member) and a second portion alignable with the plurality of markings on the front face of the alignment gauge. In operation, when the second portion of the elongate member is aligned with the plurality of markings on the front face of the alignment gauge, the operator or surgeon can determine the amount of translation (in mm) between the first bone member and a longitudinal axis running through the center of the first support member by measuring the amount of translation in an anterior-posterior plane, medial-lateral plane, for example.

DETAILED DESCRIPTION

Figure 2:
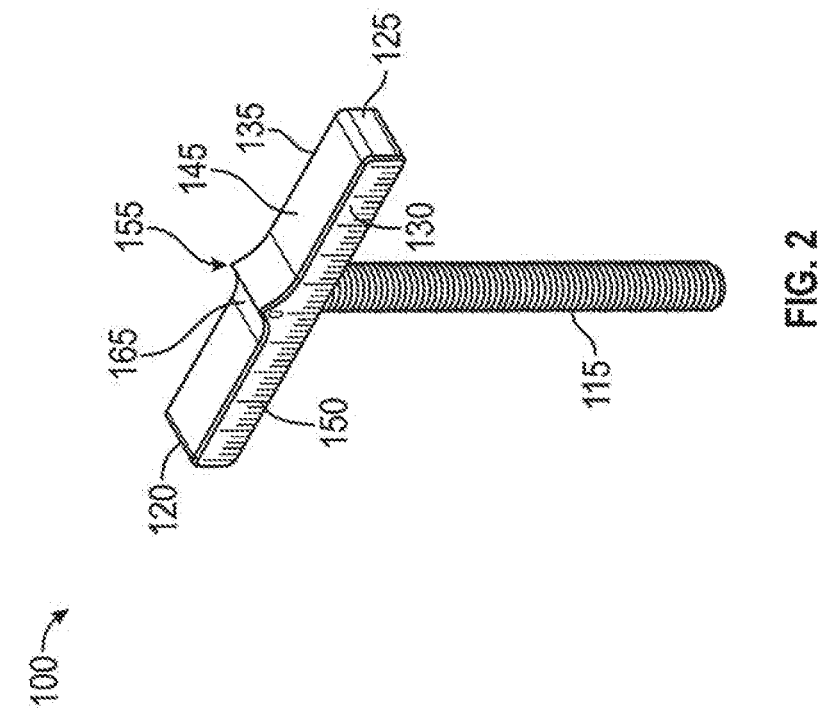
FIG. 2. is a perspective view of the alignment gauge of FIG. 1.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, and/or methods disclosed herein can be made and executed without undue experimentation in light of the present disclosure. While the articles, compositions, and methods of the inventive concept (s) have been described in terms of particular embodiments, it will be apparent to those of skill in the art that variations may be applied to the articles, compositions and/or methods and in the steps or in the sequence of steps of the methods described herein without departing from the concept, spirit, and scope of the inventive concept(s). All such similar substitutes and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/ device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with", "adjacent to", and "coupled to" include both direct association of two items to one another as well as indirect association of two items to one another. Additionally, one or more intermediary substances, compounds, tissues, fabrics, or other materials may be disposed between the two items and yet the two items are still to be considered "associated with" or "adjacent to".

Figure 1:
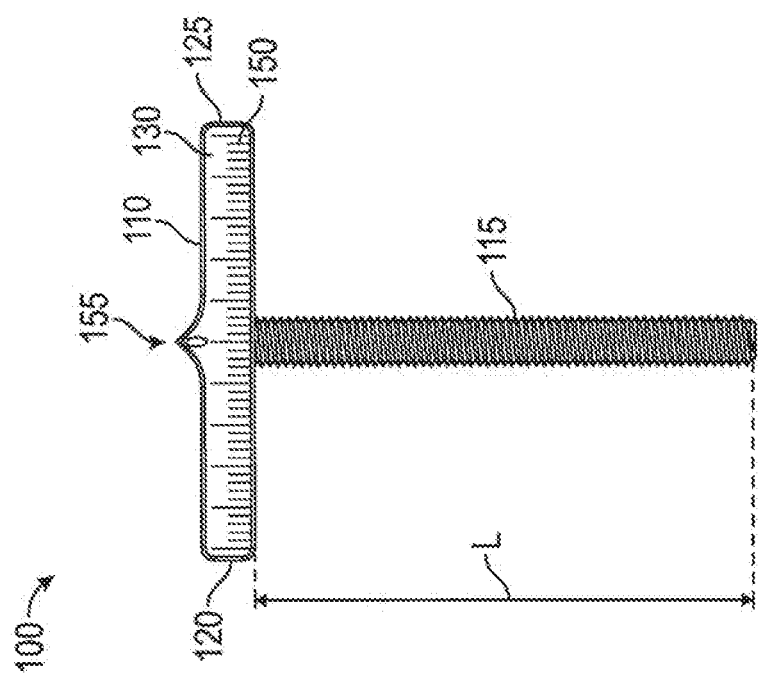
FIG. 1 is a front elevational view of one embodiment of the alignment gauge of the presently disclosed and/or claimed inventive concept(s).

An alignment gauge 100 is shown generally in FIG. 1. The alignment gauge 100 includes a body member 110 and an extension member 115. The body member 110, as can be better appreciated in FIG. 2, includes a first end 120, a second end 125, a front face 130, a back face 135, a top face 140, and a bottom face 145. The front face 130 includes a plurality of markings 150 evenly spaced across the front face 130 from the first end to the second end 125. In one embodiment, the plurality of markings 150 are spaced apart from one another in 1 mm increments with a center point 155 designated as zero to thereby form a ruler across the front face 130. As can be appreciated from FIG. 1, moving toward either the first end 120 or the second end 125 from the center point 155, the plurality of markings indicate 1 mm increments of distance away from the center point 155. By way of example, as shown in FIG. 1, a measurement that is made along the alignment gauge 100 at reference numeral A, would indicate that the measurement is 7 mm from the center point 155 toward the second end 125.

In the embodiment shown in FIGS. 1 and 2, the body member 110 further includes a protrusion 160 extending a distance away from the bottom face 145. The protrusion 160 extends the width of bottom face 145 from the front face 130 to the back face 135. The protrusion 160 is positioned on the bottom face 145 such that a tip 165 of the protrusion 160 is aligned with the center point 155 of the plurality of markings 150. The width of tip 165 extending from the front face 130 to the back face 135 is imperceptible to an observer (for example, when the body member is visualized by fluoroscopy) when the alignment gauge 100 is viewed from a front plane as shown in FIG. 1. Conversely, when the alignment gauge 100 is viewed from an oblique angle, as shown in FIG. 2, the width of tip 165 can be appreciated. The width of the tip 165 provides a visual reference as to the viewing angle of the alignment gauge 100.

As also shown in the embodiment of the body member 110 in FIGS. 1 and 2, the union of the bottom face 145 with the first end 120 and the second end 125 is sloping so as to give a more rounded or chamfered transition between the surfaces. Similarly, the union of the top face 140 with the first end 120 and the second 125 is sloping so as to give a more rounded or chamfered transition between the surfaces. As would be appreciated by one of ordinary skill in the art, the union of the top face 140 and the bottom face 145 with the first and second ends 120, 125, respectively, may occur at a right angle so as to provide a squared appearance or transition between the surfaces. It is also contemplated that the union of the top face 140 and the bottom face 145 with the first and second ends 120, 125, respectively, may occur at any angle so as to provide a profile whereby the height of the first and second ends 120, 125 is smaller (or, in an alternative embodiment not shown, is larger) than the height of the body member 110 as measured from the top face 140 to the bottom face 145.

The extension member 115 is connected to and extends from the body member 110. The extension member 115 has a length L and a longitudinal axis extending through the center of the extension member 115 that is parallel to the length L. The extension member 115 is connected to the body member 110 and the longitudinal axis of the extension member 115 aligns with the center point 155. As shown in FIGS. 1 and 2, the extension member 115 is threaded and a portion of the extension member 115 is threaded into the body member 110 via a recess (not shown) in the top face 140. In this manner, the extension member 115 is reversibly connectable to the body member 110. As will be appreciated by one of ordinary skill in the art, the extension member 115 may be threaded along its entire length, along one or more portions of its length, and/or devoid of threads entirely. In an embodiment in which the extension member 115 is devoid of threads, the extension member 115 is connected to the body member 110 via alternative means. For example, the extension member 115 may be connected to the body member 110 via glue, welds, friction fit, or the extension member 115 may be fabricated as an integral part of the body member 110 via injection molding or machining, for example.

The alignment gauge 100 may be constructed of any material suitable for use in a surgical setting. For example, in one embodiment the alignment gauge 100 is constructed from a metal such as aluminum, titanium, stainless steel, or the like. In an alternative embodiment, the alignment gauge 100 may be constructed of a non-metallic material including but not limited to polymer compositions (e.g. poly-ether-ether-ketone (PEEK) and/or poly-ether-ketone-ketone (PEKK)), ceramic, or any combination of these materials. Indeed, the body member 110 and the extension member 115 may be constructed of the same or differing materials—for example, but not by way of limitation, the body member 110 may be constructed out of PEEK while the extension member 115 is metallic. In embodiments where the body member 110 is constructed of a radiolucent material such as PEEK, it is contemplated that the plurality of markings 150 be fabricated from a radiodense or radiopaque material such that the plurality of markings 150 can be readily observable under X-ray or fluoroscopy.

Figure 4:
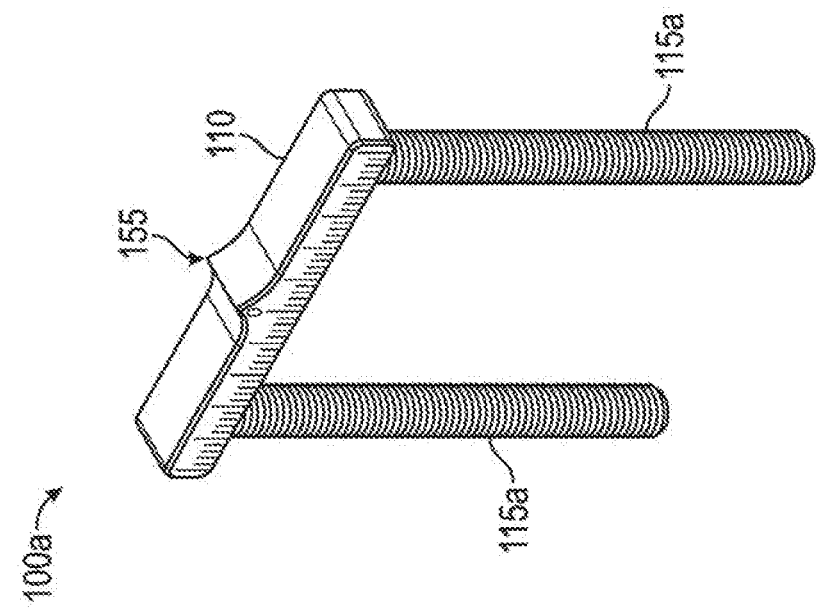
FIG. 4 is a perspective view of the alignment gauge of FIG. 3.
Figure 3:
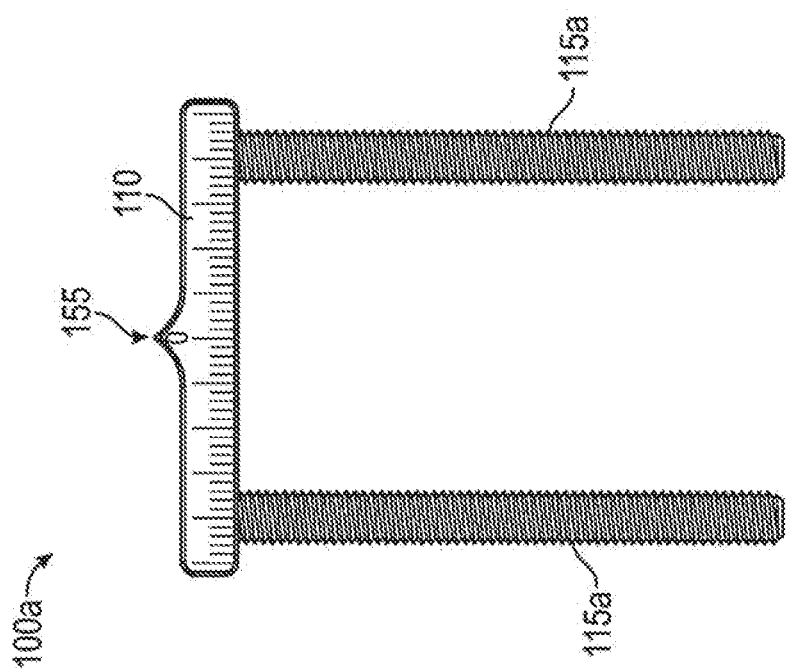
FIG. 3 is a front elevational view of an alternative embodiment of an alignment gauge.

An alternative embodiment of the alignment gauge 100 (designated as 100a) is shown in FIGS. 3 and 4 and includes body member 110 and two extension members 115a. The extension members 115a are connected to the body member 110 in a spaced apart configuration. The extension members 115a are similar to extension member 115 in size, shape, and construction. Instead of being connected to the body member 110 at the center point 155, the extension members 115a are equally spaced away from the center point 155. In the embodiment of FIGS. 3 and 4, the longitudinal axis of the extension members 115a intersects the body member 110 at a distance of 20 mm from the center point 155.

Figure 6:
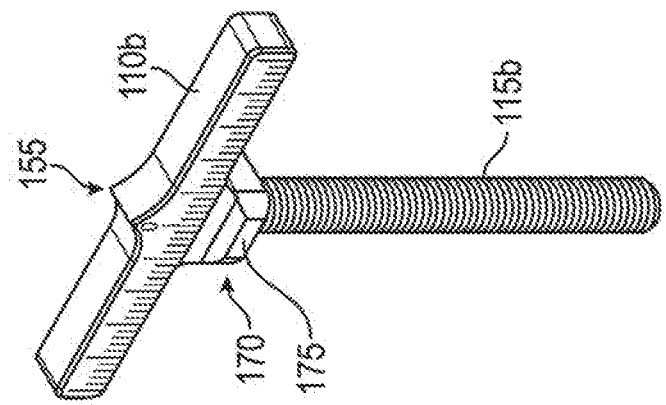
FIG. 6 is a perspective view of the alignment gauge of FIG. 5.
Figure 5:
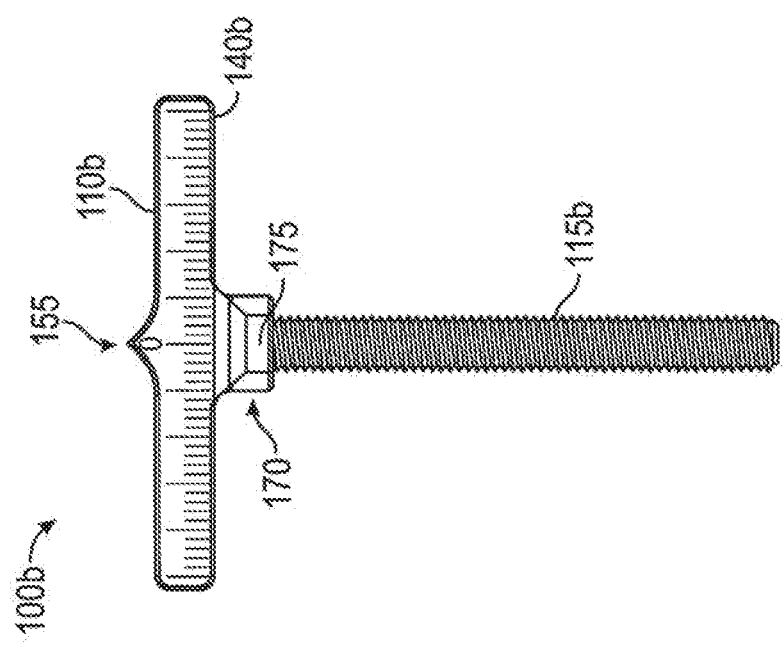
FIG. 5 is a front elevational view of an additional embodiment of an alignment gauge.

Another embodiment of the alignment gauge 100 (designated as 100b) is shown in FIGS. 5 and 6 and includes body member 110b and extension member 115b. In this embodiment, the body member 110b includes an engagement member 170 attached to and integral with the top face 140b of the body member 110b. The engagement member 170 includes two or more surfaces 175 for engagement with a wrench (not shown) or other tool capable of engaging with the surfaces 175 and applying radial torque to the extension member 115b. In this manner, the extension member 115b having threads along its length can be screwed into a correspondingly threaded receptacle. The engagement member 170 can be fabricated from the same material as the body member 110, the extension member 115, or it may be fabricated from a different material.

Figure 8:
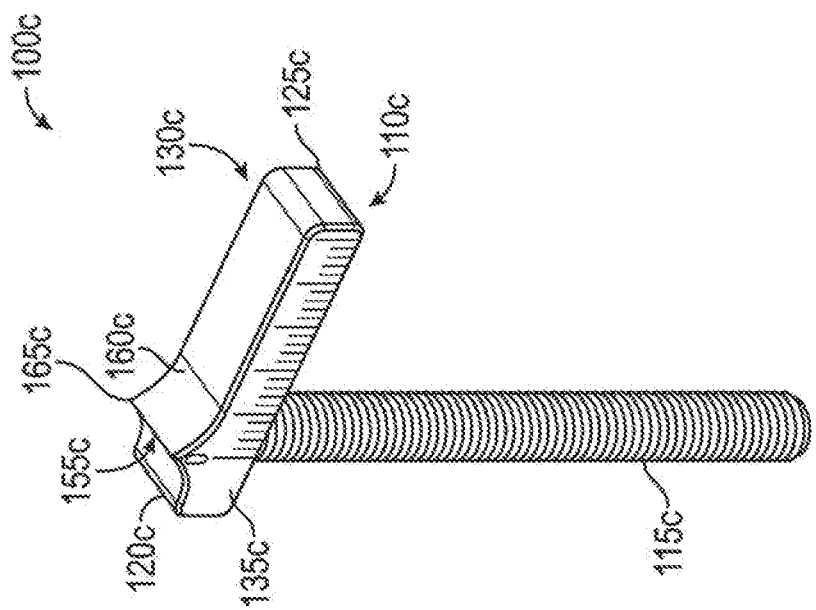
FIG. 8 is a perspective view of the alignment gauge of FIGS. 7A and 7B.
Figure 7B:
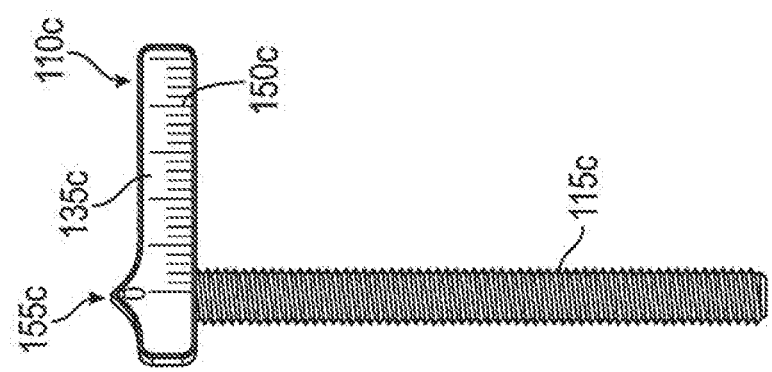
FIG. 7B is a rear elevational view of the alignment gauge of FIG. 7A.
Figure 7A:
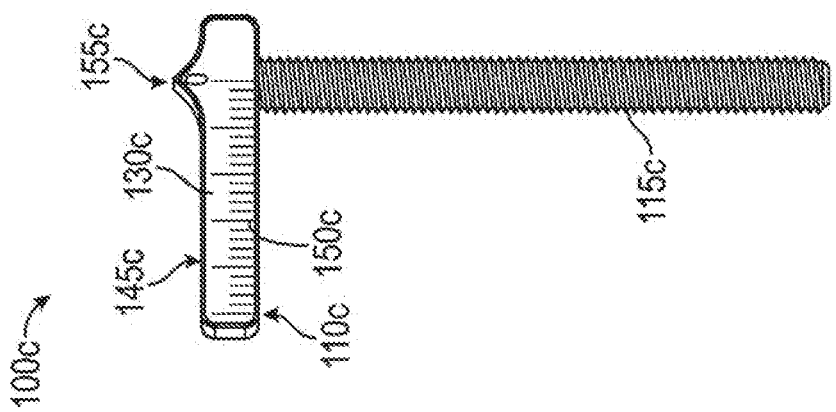
FIG. 7A is a front elevational view of another embodiment of an alignment gauge.

A further embodiment of the alignment gauge 100 (designated as 100c) is shown in FIGS. 7A-B and 8 and includes a body member 110c and an extension member 115c. The body member 110c is a truncated version of body member 110 for use in surgical applications where space may be constrained. The body member 110c has a length extending from the first end 120c to the second end 125c that is less than the length of body member 110 extending from the first end 120 to the second end 125. The front face 130c and the back face 135c have a plurality of markings 150c extending from a center point 155c. The longitudinal axis of the extension member 115c intersects the body member 110c at the center point 155c. The tip 165c of the protrusion 160c on the bottom face 145c of the body member 110c is aligned with the longitudinal axis of the extension member 115c through the center point 155c.

Figure 10:
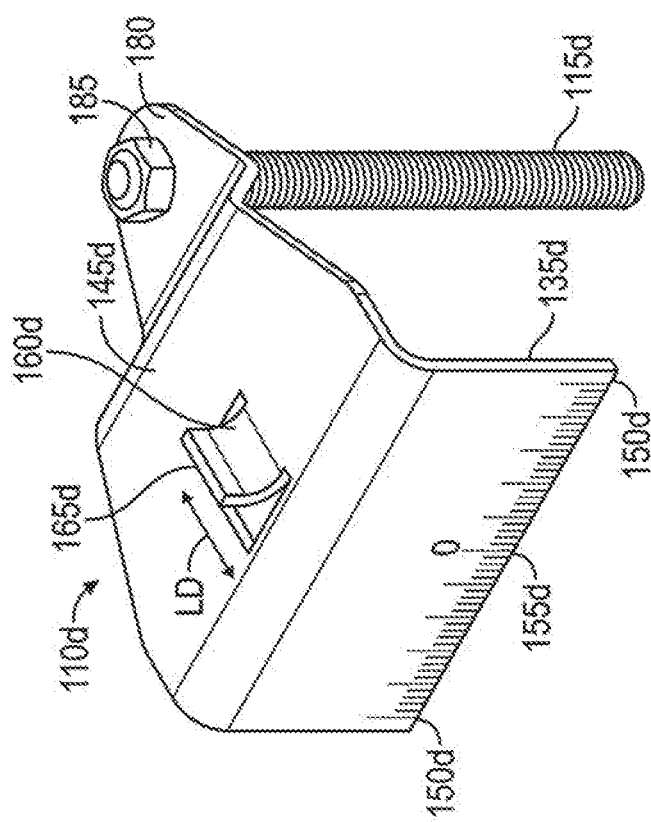
FIG. 10 is a perspective view of the alignment gauge of FIG. 9.
Figure 9:
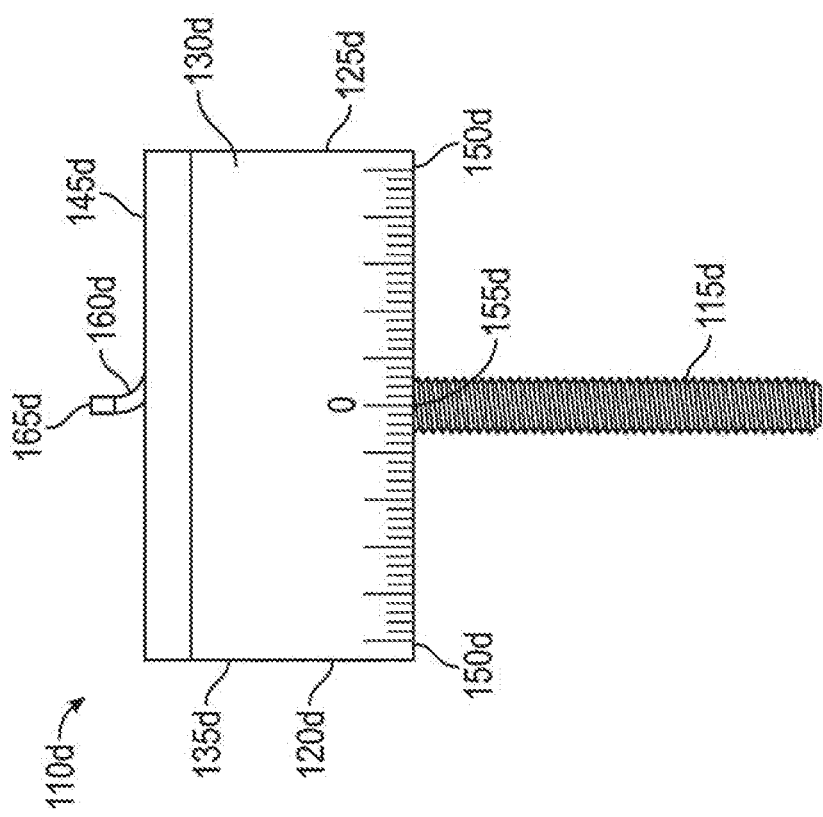
FIG. 9 is a front elevational view of an embodiment of an alignment gauge.

An embodiment of the alignment gauge 100 (designated as 100d) is shown in FIGS. 9 and 10 and includes a body member 110d and an extension member 115d. The body member 110d includes a first end 120d, a second end 125d, a front face 130d, a back face 135d, and a bottom face 145d. The front face 130d has a plurality of markings 150d extending across the front face 130d from the first end 120d to the second end 125d. The plurality of markings 150d are evenly spread across the front face 130d and designate a distance of 1 mm between each mark. As shown in FIGS. 9 and 10, the plurality of markings 150d start at the center point 155d (designated as "0") and move outwardly toward the first and second ends 120d, 125d, respectively. The protrusion 160d extends from the bottom face 145d of the body member 110d. The protrusion 160d ends in a tip 165d having a length LD. The body member 100d is connected to the extension member 115d via a connection flange 180 and at least one retaining member 185, shown as a threaded nut in FIG. 10, for example but not by way of limitation. When the body member 110d and the extension member 115d are connected, the center point 155d is in alignment with the tip 165d of the protrusion 160d as well as with a longitudinal axis centered through the length of the extension member 115d.

In operation, the alignment gauge 100 is used in conjunction with an external fixation system for the surgical treatment of fractures and bone deformities. Those of ordinary skill in the art, given the present disclosure, will appreciate that the alignment gauge 100 is especially useful in fixation systems using ring external fixation in combination with adjustable struts. For example, but not by way of limitation, one such fixation system is the TAYLOR SPATIAL FRAME® (Smith & Nephew, Memphis, Tenn.) which is based on the general concept of a Stewart platform. (See, e.g., U.S. Pat. Nos. 5,702,389, 5,728,095, 5,891,143, 5,971,984, 6,030,386, and 6,129,727, the entire contents of all of which are hereby incorporated by reference in their entirety). Another exemplary fixation system is the TL-HEX® (Orthofix, Lewisville, Tex.) external fixation system. These known fixation systems (as well as others known to those of ordinary skill in the art) combine the mechanical components of an external fixator with a computer programmed with algorithms to align fragments of a fractured bone and/or correct bone deformities, for example. It is to these external fixation systems that the alignment gauge 100 is intended for use.

Figure 11:
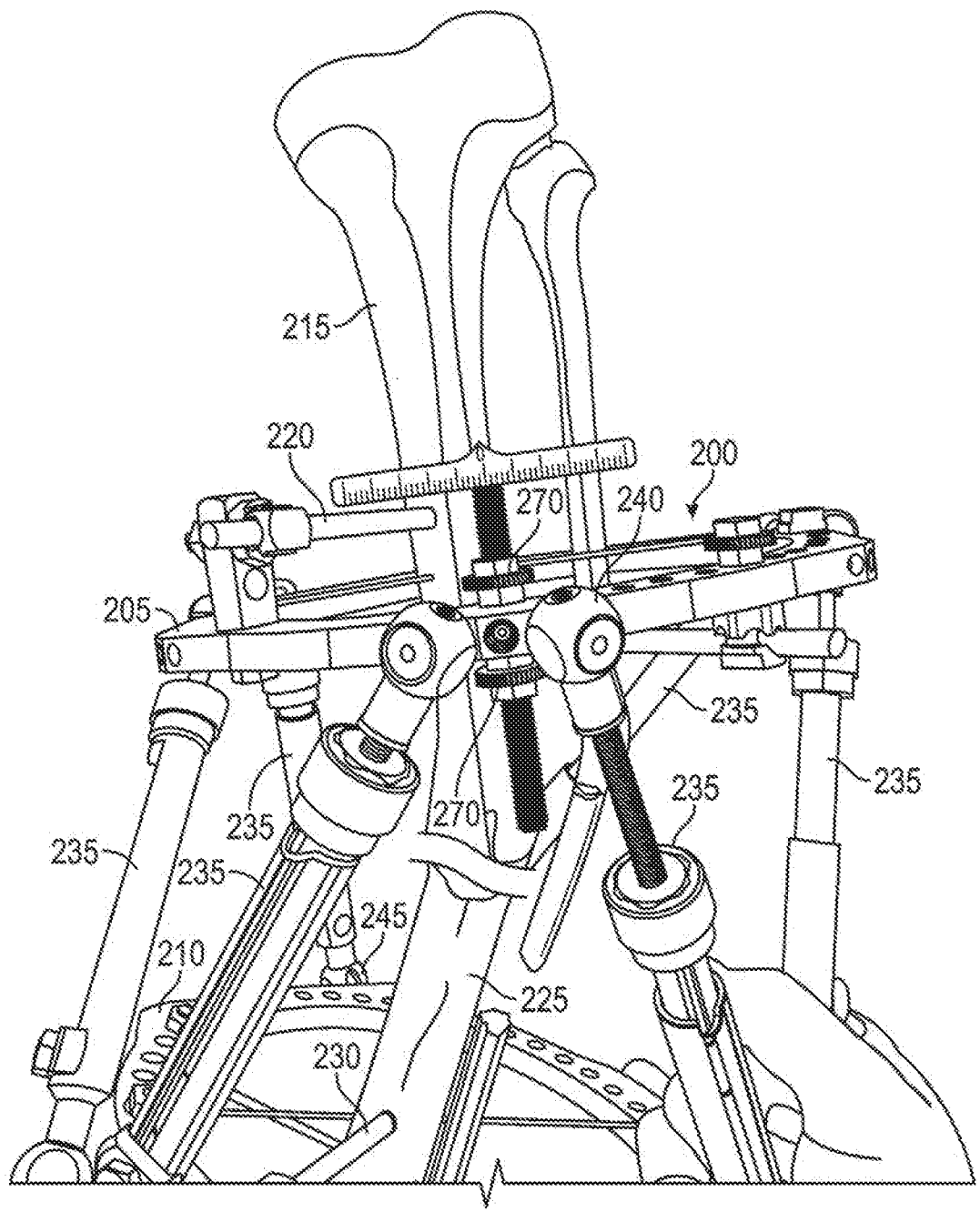
FIG. 11 is a perspective view of a fractured bone and external fixator applied thereto.

One such exemplary external fixator 200 and broken bone (a broken tibia is shown, but the broken bone can be any bone susceptible to treatment via an external fixator) is shown in FIG. 11. In particular, the external fixator 200 includes a first support member 205 and a second support member 210. The first support member 205 is a ring encircling and connected to a first bone member 215. In particular, the first support member 205 is connected to the first bone member 215 via a combination of wires and pins (for example, pin 220), both of which are well known in the art. The second support member 210 is a ring encircling and connected to a second bone member 225. In particular, the second support member 210 is connected to the second bone member 225 via a combination of wires and pins (for example, pin 230). A radial plane of the first support member 205 generally intersects and is perpendicular to a longitudinal axis of the first bone member 215 when the first support member 205 is connected to the first bone member 215. Likewise, a radial plane of the second support member 210 generally intersects and is perpendicular to the longitudinal axis of the second bone member 225 when the second support member 210 is connected to the second bone member 225. When connected to the first and second bone members 215, 225, respectively, the first and second support members 205, 210, respectively are generally not in a parallel orientation with respect to one another as shown in FIG. 11.

The external fixator 200 further includes a plurality of struts 235 with six such struts shown in FIG. 11. Each strut has a first end 240 pivotally connected to the first support member 205 and a second end 245 pivotally connected to the second support member 210. Each strut also has an adjustable length. When the first bone member 215 and the second bone member 225 are out of alignment (as shown in the fractured state of FIG. 11), at least two of the plurality of struts 235 are of different lengths. The plurality of struts 235 can be shortened and/or lengthened so as to move the second bone member 225 into alignment with the first bone member 215 and thereafter promote healing of the fracture separating first and second bone members 215, 225, respectively.

Figure 12:
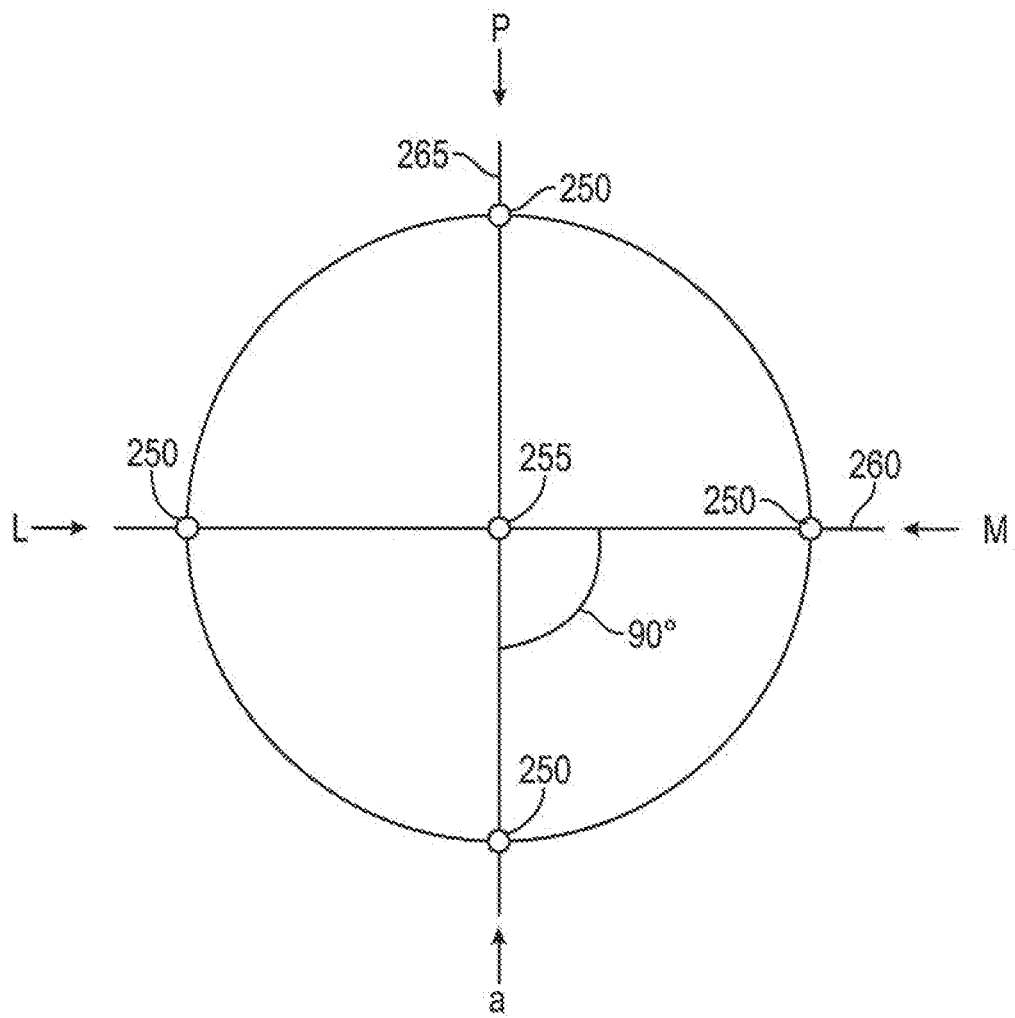
FIG. 12 is a diagrammatic representation of the center points of origin of a support member of a support member of an external fixator.

Once applied to the first and second bone members 215, 225, respectively, the plurality of struts 235 are manipulated so as to put the bone members into alignment. Such manipulation is a complicated process involving high level mathematics and spatial programming. Computer software has been developed to facilitate the manipulation of the plurality of struts 235 and thereafter bring the broken bones into alignment. The computer software generally requires certain inputs in order to manipulate and adjust the plurality of struts 235—for example, the software requires knowledge of the spatial placement and orientation of at least one of the first and second bone members 215, 225, respectively, with respect to the corresponding first and second support members, 205, 210, respectively. In the embodiment shown in FIGS. 11 and 13, the first support member 205 includes a plurality of origin points 250. The plurality of origin points 250 are spaced equidistant around the first support member 205 and are positioned on the first support member 205 where a first ray 260 and a second ray 265, extending outwardly from a center point 255 within an area defined by the first support member 205, intersects the first support member 205. As shown in FIG. 12, the first and second rays 260, 265 are at a right angle to one another. As such, the plurality of original points 250 each are generally adjacent an apex of the first support member 205 when viewed on edge from an anterior (a), posterior (p), lateral (l), and/or medial (m) position.

The alignment gauge 100 facilitates the measurement of an amount of translation (in mm) between the center point 255 of at least one of the first and second support members 205, 210 and a central longitudinal axis of at least one of the first and second bone members 215, 225. The amount of translation measured indicates the position of the longitudinal center axis of the first and second bone members 215, 225 within the first and second support members 205, 210. In order to generate a prescription or set of instructions for adjusting the struts 235 to thereby bring the first and second bone members 215, 225 in alignment, certain data points must be provided to the software. For example, the data points may include: the bone fragment that is to be measured (i.e., the proximal or distal bone fragment); the lengths of the struts as applied to the bone fragments, various reference measurements with respect to the deformity, and spatial measurements as to the placement of the bone fragment within the support member.

In current practice, the process of determining the amount of translation distance between a central longitudinal axis of at least one bone fragment and a center point of at least one support member is error-prone. Oftentimes, the surgeon is required to estimate this translational distance from an X-ray or radiograph that is likely to be partially or completely obscured by the metallic elements of the external fixator. Incorrect measurements of this translational distance results in an incorrect alignment "prescription" being generated by the computer system. The result being a misalignment of the bone fragments.

Figure 13:
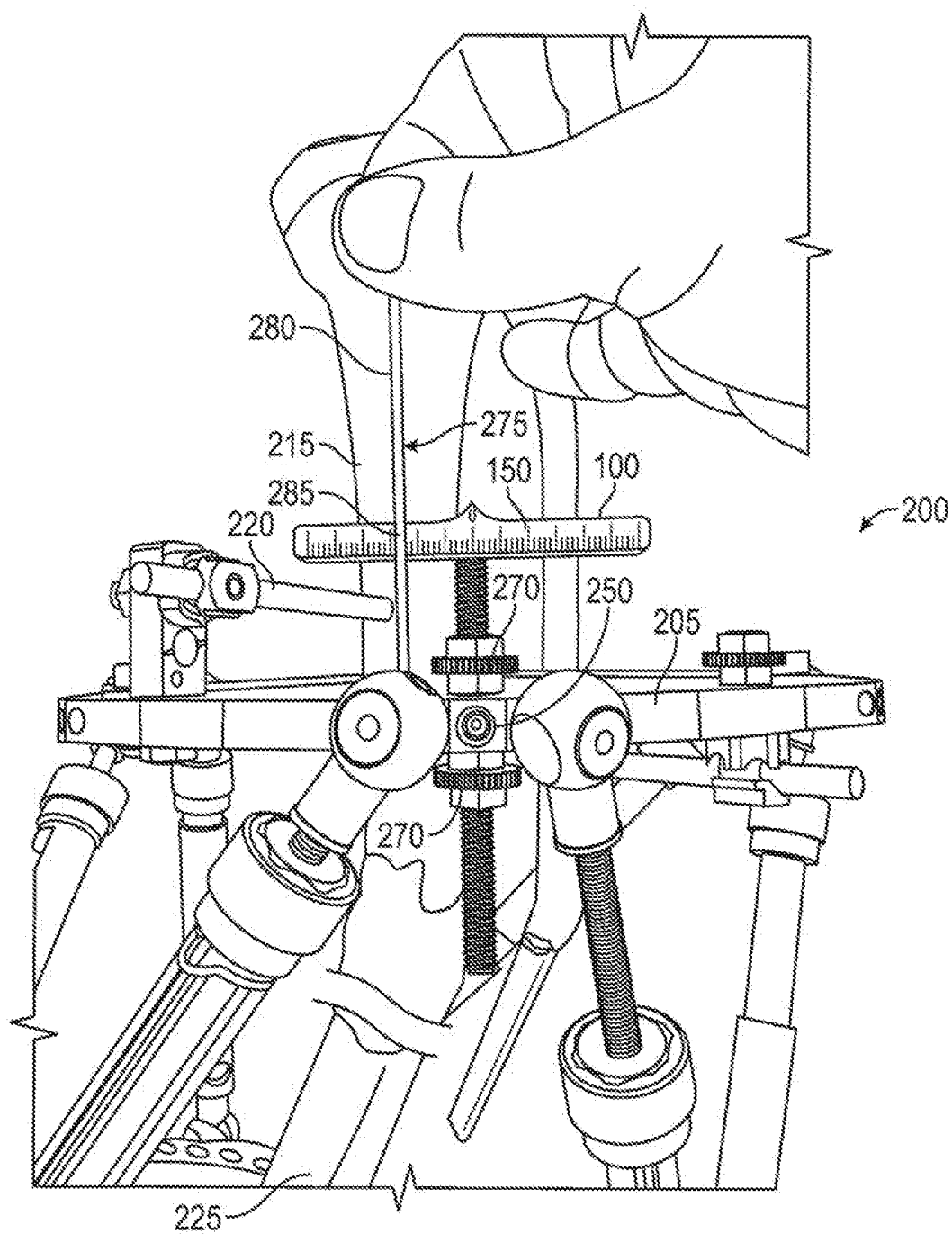
FIG. 13 is a perspective view of a fractured bone, external fixator, and the alignment gauge of FIG. 1 being used to measure the translational distance between the bone fragments in an anterior-posterior plane.

In order to obtain the translational distance between the central longitudinal axis of the first bone member 215 and the center point 255 of the first support member 205, the alignment gauge 100 is attached to the external fixator 200 as shown in FIGS. 11 and 13. In particular, the alignment gauge 100 is attached to first support member 205 via a threaded distal end of the extension member 115. The extension member 115 is connected to the first support member 205 via attachment members 270 and, when connected, the longitudinal axis of the extension member 115 is aligned with the respective origin point 250 of the first support member 205 with which it is associated. The alignment gauge 100, as shown in FIGS. 11 and 13, extends away from the first support member 205. Alternatively, the alignment gauge 100 can be connected to the first support member 205 such that the tip 165 of the protrusion 160 points generally toward the second support member 210. The external fixator 200 and first and second bone members, 215, 225, respectively, are positioned such that an AP view is obtained from a fluoroscope. A radiopaque elongate member 275 (for example, a K-wire, a metal tube, or other thin radiopaque object) is introduced and a first portion 280 of the elongate member 275 is aligned with the central longitudinal axis of the first bone member 215 and a second portion 285 of the elongate member 275 is overlaid and aligned with the plurality of markings 150 on the front face 130 of the body member 110.

The specific indicia of the plurality of markings 150 over which the second portion 265 of the elongate member 275 is overlaid or adjacent is the amount of translational distance (from an AP view) between the central longitudinal axis of the first bone member 215 and the center point 255 of the first support member 205. In the specific example shown in FIG. 13, the amount of translational distance between the central longitudinal axis of the first bone member 215 and the center point 255 of the first support member 205 is 13 mm.

Similarly, the amount of translational distance between the central longitudinal axis of the first bone member 215 and the center point 255 of the first support member 205, as viewed from a lateral perspective, is also determined. The alignment gauge 100 is removed from the origin point 250 in the AP plane and connected to a second origin point 250 on the first support member 205 at a lateral position. The external fixator 200 and first and second bone members, 215, 225, respectively, are positioned such that a lateral view is obtained from a fluoroscope. The radiopaque elongate member 275 is reintroduced and the first portion 280 of the elongate member 275 is aligned with the central longitudinal axis of the first bone member 215 and the second portion 285 of the elongate member 275 is overlaid and aligned with the plurality of markings 150 on the front face 130 of the body member 110. As with the AP view, the specific marking of the plurality of markings 150 over which the second portion 265 of the elongate member 275 is overlaid or adjacent is the amount of translational distance (from a lateral view) between the central longitudinal axis of the first bone member 215 and the center point 275 of the first support member 205. Once the AP and lateral translational distances of the central longitudinal axis of the first bone member 215 is known, these values are provided to the computer program which calculates the position and alignment of the first bone member 215 with respect to the first support member 205. In combination with other variables provided by the operator/surgeon, the software thereafter provides a "prescription" for incrementally changing the length of the plurality of struts 235 to thereby align the first and second bone members 215, 225, respectively.

As would be appreciated by one of ordinary skill in the art, while only two translational measurements are described with respect to the first bone member 215 and the first support member 205, the alignment gauge 100 can be moved to at least one of the other origin points 250 and translational distances can be measured as described above. In this manner, the measurements of translational distance can be compared and confirmed. Further, while the measurement of the translational distance has been described hereinabove as being conducted with respect to first bone member 215 and the first support member 205, one of ordinary skill in the art will appreciate that the methodology can be used to alternatively or additionally measure the translation distance with respect to the second bone member 225 and the second support member 210.

In obtaining the AP and lateral views for making an accurate determination of translational distance, maintaining the fluoroscope in a configuration substantially perpendicular to the plane of the front face 130 of the body member 110 is preferred. If the fluoroscope is at a greater than or less than a 90-degree angle with respect to the front face 130 of the body member 110, inaccurate translational distance measurements will be obtained. The alignment gauge 100 is configured to visually alert an operator as to any such misalignment of the fluoroscope with the front face 130 of the body member 110. In particular, the length LD of the tip 165 of the protrusion 160 on the body member acts as a visual indicator of correct fluoroscope alignment. If the length LD of the tip 165 is visible via fluoroscope (for example, the length of the tip 165 appears as shown in FIG. 2), the focal plane of the fluoroscope is not parallel with the plane of the front face 130 of the body member 110 and an accurate measurement cannot be taken. Conversely, if the length LD of the tip 165 cannot be seen via fluoroscope (for example, the length LD of the tip 165 cannot be seen as shown in FIG. 1), the focal plane of the fluoroscope is parallel with the plane of the front face 130 of the body member 110 and an accurate translational measurement can be made. In this way, the length LD of the tip 165 acts as a visual check as to the correct placement and/or alignment of the fluoroscope with respect to the front face 130 of the body member 110 of the alignment gauge 100.

Thus, in accordance with the presently disclosed inventive concept(s), there have been provided devices, as well as methods of producing and using same, which fully satisfy the objectives and advantages, set forth hereinabove. Although the presently disclosed inventive concept(s) has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the presently disclosed inventive concept(s).

The invention claimed is:

1. An external fixator, comprising:
   a first support member connectable to a first bone member;
   a second support member connectable to a second bone member;
   a plurality of struts, each strut having one end pivotally connected to the first support member, another end pivotally connected to the second support member, and an adjustable length; and
   an alignment gauge connected to the first support member, the alignment gauge comprising:
   a body member having a first end, a second end, a front face, a back face, a top face, and a bottom face, at least the front face having a plurality of markings, the body member supported by the first support member adjacent the first bone member; and
   an elongate member having a first portion alignable with the first bone member and a second portion alignable with the markings on the front face of the body member to provide a visual indication of the relative position of the first bone member to the first support member.

2. The external fixator of claim 1, wherein the bottom face of the body member has a protrusion defining a center line of the body member.

3. The external fixator of claim 1, wherein the body member has a thickness extending between the front face and the back face and a height extending between the top face and the bottom face, and wherein the thickness is substantially the same as the height.

4. The external fixator of claim 1, wherein the alignment gauge further comprises an extension member having one end connected to the body member and another end connected to the first support member.

5. The external fixator of claim 4, wherein the distance between the body member and the first support member is adjustable.

6. An alignment gauge for an external fixator having a first support member connectable to a first bone member, a second support member connectable to a second bone member, a plurality of struts pivotally connected to the first support member and the second support member, the alignment gauge comprising:
   a body member having a first end, a second end, a front face, a back face, a top face, and a bottom face, at least the front face having a plurality of markings, the body member connectable to the first support member of the fixator in a way that the body member is adjacent the first bone member; and
   an elongate member having a first portion alignable with the first bone member and a second portion alignable with the markings on the front face of the body member to provide a visual indication of the relative position of the first bone member to the first support member.

7. The alignment gauge of claim 6, wherein the bottom face of the body member has a protrusion defining a center line of the body member.

8. The alignment gauge of claim 6, wherein the body member has a thickness extending between the front face and the back face and a height extending between the top face and the bottom face, and wherein the thickness is substantially the same as the height.

9. The alignment gauge of claim 6, further comprising an extension member having one end connected to the body member and another end connectable to the first support member.

10. The alignment gauge of claim 9, wherein the distance between the body member and the first support member is adjustable.

11. A method for measuring a translation distance between a first bone member and a center point of a first support member, comprising:
    attaching a first support member to a first bone member, the first bone member having a central longitudinal axis extending through the first bone member and the first support member having a center point within the area defined by the first support member;
    attaching an alignment gauge to the first support member and adjacent the first member, wherein the alignment gauge has a body member having a first end, a second end, a front face, a back face, a top face, and a bottom face, at least the front face having a plurality of markings, the body member attached to the first support member in a way that the body member is adjacent the first bone member;
    placing an elongate member having a first portion alignable with the central longitudinal axis of the first bone member and a second portion alignable with the markings on the front face of the body member; and
    measuring a translational distance between the central longitudinal axis of the first bone member to the center point of the first support member.

12. The method of claim 11, wherein the bottom face of the body member has a protrusion defining a center line of the body member.

13. The method of claim 12, wherein the center line of the body member is aligned with the center point of the first support member.

14. The method of claim 11, wherein the body member has a thickness extending between the front face and the back face and a height extending between the top face and the bottom face, and wherein the thickness is substantially the same as the height.

15. The method of claim 11, wherein the body member further comprises an extension member having one end connected to the body member and another end connectable to the first support member.

16. The method of claim 15, wherein the distance between the body member and the first support member is adjustable.

* * * * *